Jan. 23, 1951 F. H. MONTMARQUET Re. 23,334

ATHLETIC SUPPORTER

Original Filed June 19, 1942 2 Sheets-Sheet 1

INVENTOR.
FRANCIS H. MONTMARQUET
BY
J. F. Bassecheas
his ATTORNEY

ATHLETIC SUPPORTER

Original Filed June 19, 1942 2 Sheets-Sheet 2

INVENTOR.
FRANCIS H. MONTMARQUET
BY
J. F. Bassuches
his ATTORNEY

Reissued Jan. 23, 1951

Re. 23,334

UNITED STATES PATENT OFFICE 23,334

ATHLETIC SUPPORTER

Francis H. Montmarquet, Little Falls, N. J.

Original No. 2,301,066, dated November 3, 1942, Serial No. 447,658, June 19, 1942. Application for reissue June 17, 1950, Serial No. 168,819

4 Claims. (Cl. 128—158)

Matter enclosed in heavy brackets [ ] appears in the original patent but forms no part of this reissue specification; matter printed in italics indicates the additions made by reissue

This invention relates to an athletic supporter generally referred to as a jock strap. More particularly, my invention relates to the novel interrelationship of belt and sack elements of an athletic supporter.

My invention is directed to a jock strap construction or athletic supporter comprising a sack portion, a belt portion and leg straps in which the elements are combined in order to secure maximum comfort and proper support during violent exercise, while effecting the greatest amount of economy in respect of the materials entering into the combination.

In suspensory bandages or supports known to me, efforts have been made to provide comfort in attaching the sack to the supporting belt by suspending elements following generally the line of the groin. These devices being intended primarily to alleviate a distressed condition, were not designed for protection during violent exercise. Endeavors to accommodate such a device as known to me with angularly directed groin conforming supports involved intricate braces and straps which introduced elements of cost with regard to workmanship and materials.

In the production of relatively inexpensive athletic supporters or jock straps involving webbing constituting the belt and a pouch portion of fabric of knitted elastic material, or constructions intended to support a protective cup, resort to elastic webbing of from two to three inches in width embraced such material sections of the body as to be readily displaced, requiring constant attention during violent exercise, to reposition the pouch which the belt portion suspends, and which becomes displaced in exercise. The characteristic gesture to accomplish this replacement is well known.

Accordingly, it is an object of my invention to provide an athletic supporter in which a pouch member is supported by a relatively wide webbing and in which comfort and protection are provided, without displacement during exercising. Further objects of my invention reside in the provision of an athletic supporter or jock strap made of relatively wide webbing, in which the pouch member is supported without any tendency to "creep" or be displaced, with a consequent discomfort in the crotch, and without any tendency of the pouch member to collapse and bind within the crotch, assuring an envelopment of the organs with proper support, avoidance of accidental displacement, while retaining simplification of construction and materials, to effect great economies in workmanship and materials.

To attain these objects and such further objects as may appear herein or be hereinafter pointed out, I make reference to the accompanying drawing, forming a part hereof, in which—

Figure 1:
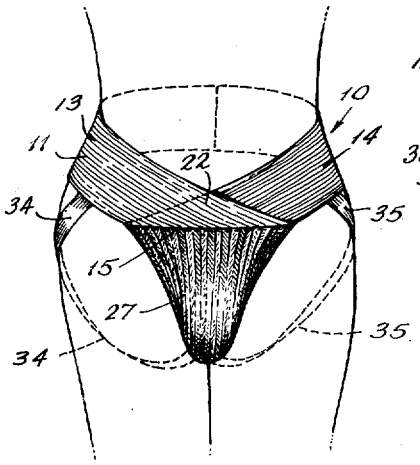
Figure 1 is a perspective view of my invention illustrated in the form in which it might appear on the torso of the wearer.
Figure 2:
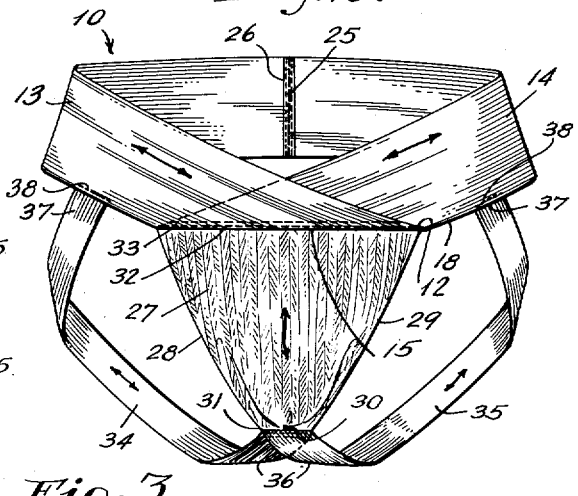
Figure 2 is a magnified plan view thereof, with the parts flattened out to show the relative arrangements.
Figure 3:
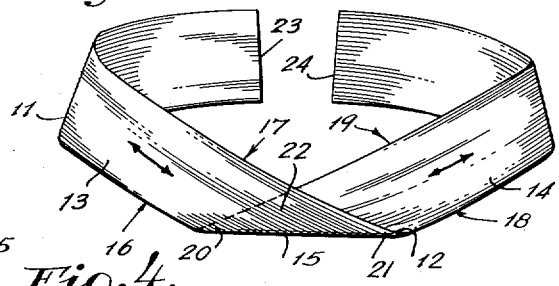
Figure 3 is a fragmentary perspective view of the belt webbing entering into the construction of the embodiment illustrated in Figures 1 and 2.

Making reference to the drawing, I have illustrated in Figures 1 to 3, a jock strap 10 comprising a belt portion 11, preferably made of a relatively wide webbing of elastic fabric approximately three inches in width in the quiescent state, with the elastic threads or cords in the warp direction. This is well known webbing material wherein elastic warp threads appear closer together adjacent the selvage than along the medial line of the webbing. The appearance of this fabric is the same on both sides.

With a length of this webbing material thus provided, I form an angular or mitre fold 12 adjacent the mid-portion thereof, forming branches 13 and 14, angularly directed towards each other and forming a straight edge 15 common to both branches, at an obtuse angle to the edge 16 and an acute angle to the edge 17 of the webbing.

A fold of this kind will result in the edge 17 of the branch 13 appearing at the upper part thereof and continuing to the bottom edge 18 of the branch 14. Likewise, the edge 16 will be lowermost in the branch 13 and will be directed to form the upper edge 19 of the branch 14.

The oppositely directed apices 20 and 21 form a triangular section 22 in overlapping relationship. The mitre overlap and the angular direction of the webbing to the edge 15 are calculated to correspond to the distance between the left and right groins approximately adjacent the crest of the pubis, for purposes which will appear more clearly as this description proceeds.

The free edges 23 and 24 are joined at the stitch line 25 and then covered with a reinforcing tape 26 by stitching the same over the seam formed by joining the edges 23 and 24 to each other.

The section thus described forms a belt element.

I then provide a pouch 27, preferably made of elastic knitted fabric having one or more elastic cords knitted lengthwise or in a warp direction adjacent the selvage edges 28 and 29. A form fitting contour is given to the webbing of which the pouch is made by seaming together at 30 one edge 31 of this fabric. The free edge 32 of the pouch webbing is then stitched to the edge 15 of the belt element previously described by the stitch lines 33 in overlapping relationship. Over this free edge a protective tape is sewn to cover the same and provide a facing.

The webbing of which the pouch 27 is formed is likewise calculated to be of a width so that in its quiescent condition it substantially corresponds to the distance between the left and right groins approximately adjacent the crest of the pubis.

I then provide leg straps 34 and 35, which are preferably formed of elastic webbing. Elasticity may be derived from rubber threads woven in the warp direction of the webbing or by utilizing knitted material or a knitted material in which elastic threads are employed. The lower terminal edges 36 of the leg straps 34 and 35 are affixed to the edge 31 of the pouch, the upper edges of which 37—37 are affixed by stitching 38—38 to the edges 16 and 18, respectively, of the belt element 11 in close adjacency to the opposite ends of the edge 15, defining the side edges of the pouch.

With a garment as thus provided, it will be observed that the pouch portion first may be made of a length of material which is shorter than that heretofore deemed necessary since support for the pouch is directed along the groin. The overlapping apices defining the triangular section 22 act as a brace, holding the sack from "breaking" and therefore assure a form fitting contour by spreading the sack adjacent the crest of the pubis from the left groin to the right groin.

The downwardly directed segments 13 and 14 adjacent the bottom edges 16 and 18 are supported substantially in the groin, holding the belt supported upon the hip bones and thereby relieving the tension on the more sensitive abdominal portions of the body between the crests of the ilium, in the abdominal cavity. The angularly directed sections above the crest of the pubis, immediately above the triangular section 22, are left unconfined by the belt portion so that violent exercise will not tend to displace the support for the pouch or increase the tension, with consequent discomfort to the wearer.

By angularly directing the branches 13 and 14 towards each other and affixing the same in overlapping position to the upper end of the pouch, the abdominal pressure substantially above the crest of the pubis is avoided and the displacing tendency of the pouch is overcome.

By attaching the belt webbing at an angle, to have the apices overlapping and criss-crossed over the longitudinal axis of the pouch, a cross pull is effected, tending to cup the pouch into form-fitting position about the organs and the pubis.

Figure 5:
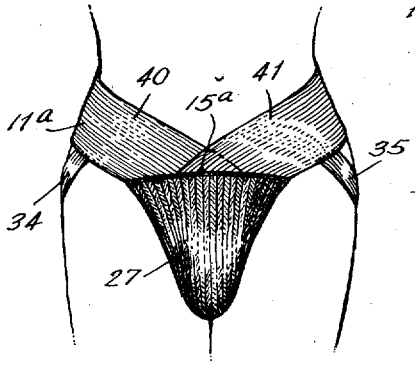
Figure 5 is a perspective view showing the embodiment of Figure 4 upon the torso of a wearer.
Figure 4:
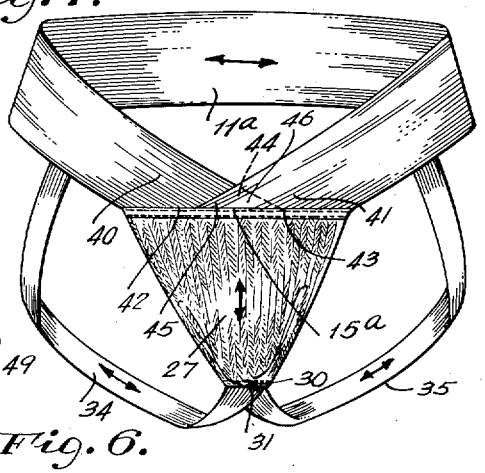
Figure 4 is a plan view of another embodiment of my invention.

In Figures 4 and 5 I have shown another embodiment of my invention wherein the belt element 11a has its terminal edges 40 and 41 formed with mitred edges 42 and 43, respectively, to provide a suspending edge 15a for the sack 27. Here the apices 44 and 45 overlap to form the triangular reinforcing section 46. Like parts are similarly numbered as in the embodiment illustrated in Figures 1 to 3.

In this embodiment, substantially all of the benefits of the embodiment illustrated in Figures 1 to 3 are achieved to a degree, with no seam adjacent the back of the garment.

Figure 6:
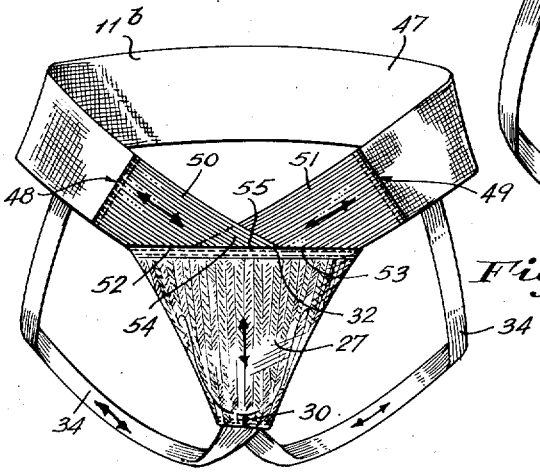
Figure 6 is a plan view of a still further embodiment of my invention.

In Figure 6 I have shown another embodiment of my invention in which the belt 11b constitutes an inelastic section 47, terminal edges of which, 48 and 49, are seamed to elastic segments 50 and 51, respectively. The sections 50 and 51 have their terminal edges formed angularly at 52 and 53, with the apices overlapping to define the triangular section 54. The overlapping angular terminals 52 and 53 define a substantial straight edge 55, to which the upper edge 32 of the pouch 27 is affixed by stitching or the like.

In this embodiment, the suspension heretofore emphasized is secured. However, great economy in elastic webbing is effected. While the webbing 47 is made of inelastic material, the angular direction of the terminal portions 48 and 49, as secured by the sections 50 and 51, serves to suspend the sack from the hips and the crest of the ilium, without discomfort and without substantial loss of support for the pouch. The angular direction at which the terminal portions of the webbing is cut so that one side of the webbing will correspond substantially to one half of the width of the pouch to which it is attached will serve to secure a gentle uplift of the pouch and an adequate anchorage of the garment over the hips and the crest of the ilium.

This type of construction, as well as my prior described embodiments, make it unnecessary to use elastic at the top edge of the pouch since the form-fitting quality adjacent this portion of the body between the groins is secured.

Figure 7:
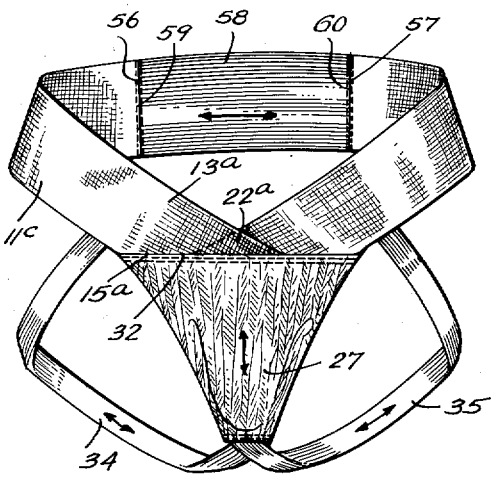
Figure 7 is a plan view of a still further embodiment of my invention.

In the embodiment illustrated in Figure 7, I have shown a belt portion 11c formed of inelastic webbing 1a, formed at the front with mitre edges for each branch, in accordance with the form shown in Figure 4, the opposite edges of each branch leaving rectangular terminal edges 56 and 57 at the rear, to which an elastic section 58 may be affixed by stitching along the seam lines 59 and 60, to opposite ends thereof.

In this view, like numerals are applied to parts corresponding to those in the prior embodiments, and therefore, further reference will not be made to the manner in which the lower edge of the pouch 27 is affixed by the leg straps to the belt portion.

In this construction the pouch 27 has its upper edge 32 stitched to the edge 15a formed by the mitre fold, as in the embodiment illustrated in Figure 2. It will be understood, however, that the left and right branches forming the belt element 11c may be two separate sections of the webbing, to provide overlapping apices defining a triangular section 22a.

Figure 8:
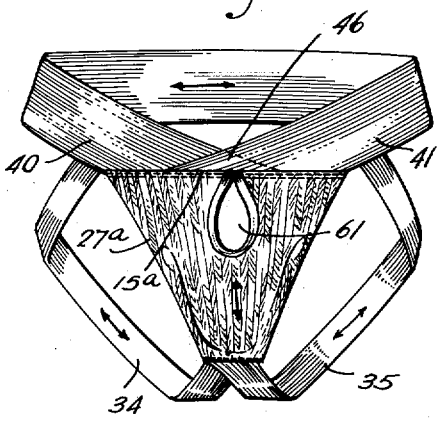
Figure 8 is a plan view of an embodiment of my invention comprising a combined suspensory and jock strap.

In the embodiment illustrated in Figure 8, I have shown a combination jock strap and suspensory wherein the pouch 27a is provided with the usual opening 61.

In all other respects, this construction may embody the suspension for the pouch by forming the belt portion thereof in accordance with any one of the forms previously described, whether a mitre fold is used for the entire belt, as illustrated in Figure 3, the overlapping apices as shown in Figure 4, or the combination of inelastic webbing and elastic webbing, as shown and described in connection with Figures 6 and 7.

Figure 9:
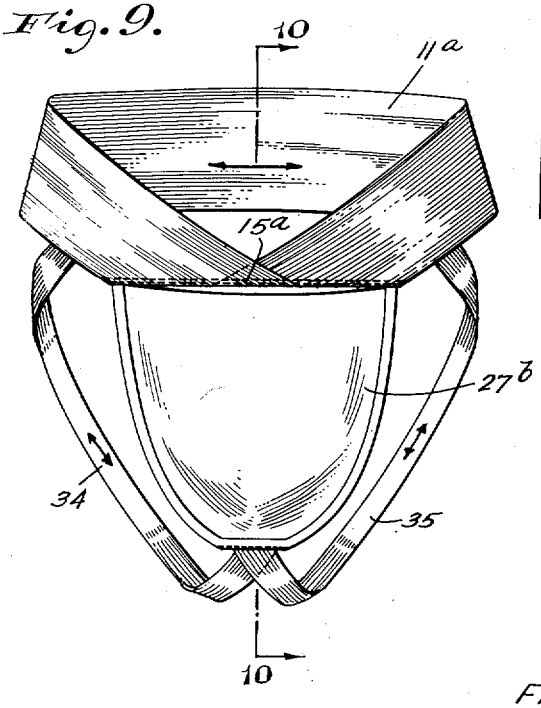
Figure 9 is a plan view illustrating my invention in the form of an athletic supporter and protective cup holder.
Figure 10:
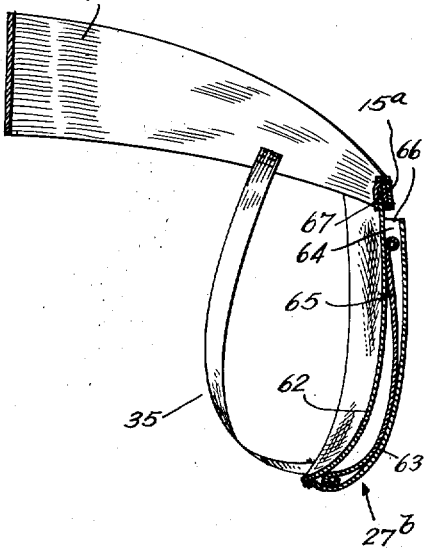
Figure 10 is a section taken on the line 10—10 of Figure 9.

In Figures 9 and 10 I have illustrated an athletic supporter in accordance with my invention, where used to hold a protective cup. In this construction, the pouch portion 27b is formed from double-layered material 62 and 63 defining a pocket 64, into which may be disposed a protective cup 65 through the opening 66. The fabric of which the sections 62 and 63 are formed is preferably inelastic material, such as Canton flannel.

The general construction of pocket and cup is preferably of the type shown in my Patent No. 2,266,062, granted December 16, 1941. The inner layer 62 has its terminal edge 67 affixed to the lower edge 15a of the belt 11a which, in all respects, may follow the construction referred to in connection with the embodiment illustrated in Figure 4. The straps 34 and 35 may be affixed to the pouch and belt, as in the prior embodiments.

In the embodiment illustrated in Figures 9 and 10, the suspension for the pouch, as effected by the belt construction which I have devised serves to center the pouch and hold the protective cup in centered position between the groins by the tension which is applied to the left and right edges of the pouch, drawing these edges into the groin and about the protective cup located in the pocket of the pouch, in accordance with this embodiment.

It will be observed that in the embodiment illustrated in Figure 4, and which may be applied in whole or in part to the embodiments illustrated in Figures 7, 8 and 9, wherein the webbing of the waistband or belt is formed with a suspending edge for the sack defined by the mitred edges of the waistband or belt elements at this point, that the degree of overlap of the apices 45 and 46 formed adjacent the suspending edge for the sack determines the degree of reinforcement. While contiguous arrangement of the apices will provide a suspending edge for the sack, the overlap is increased as reinforcement may be found necessary, and where the diagonal pull to secure a form-fitting effect is to be increased, the maximum limits being secured where a mitre fold is made in accordance with the embodiment illustrated and described in connection with Figure 3, wherein a continuous length of webbing is provided at least adjacent the upper edge of the sack.

It will further be observed that where the scrotum sack is made of elastic fabric, described as preferred in the embodiments illustrated in Figures 1 to 8, with the elasticity in a vertical direction, the angular distension in the direction of the groin, as effected by the waistband or belt element, serves as an accessory to the elasticity of the scrotum sack or pouch, and where the waistband or belt is made of elastic webbing, the distension in the fabric of the pouch or sack is minimized, with greater comfort to the wearer.

It will further be observed that by my construction torsional displacement of the waistband or belt elements from a predetermined angular position is avoided and the desired position maintained by the webbing mitred edges serving as a suspension for the upper edge of the pouch or sack in that the edges of the webbing and the upper edge of the pouch or sack cooperate with each other and the leg straps to direct the stresses in a direction to balance the forces holding the device in position. The supporter is therefore held in position against ready displacement in a simple manner, involving the minimum amount of labor and effecting economy of materials in the assembly.

In general, it will be observed that I have provided an athletic supporter which is easily manufactured and effects considerable economies in material, which has highly desirable attributes in the comfort it provides for its intended purpose, holding the organs enveloped, with the proper distribution of elasticity between the related immovable parts of the body and the crests of the ilium, whereby violent exercising may be practiced while wearing the garment, with a minimum tendency for displacement and consequent discomfort and annoyance.

Having thus described my invention and illustrated its use, what I claim as new and desire to secure by Letters Patent is:

1. An athletic supporter comprising a waistband or belt element of relatively wide *elastic* webbing, the frontal portion whereof is defined by *downwardly*, angularly directed branches formed of *said* webbing [material], said angularly directed branches *overlapping and criss-crossing each other and* defining a continuous edge common to both branches along an obliquely directed section transverse of the webbing, *along which continuous edge the sections are united by stitches, leaving the overlapping and criss-crossing portions above the common edge substantially free for relative movement of one branch to the other along the length of the webbing*, a [sack or] pouch, the upper edge of which is affixed to said continuous edge of said branches, and leg straps connecting the lower portion of said pouch to said waistband, *to direct the stresses holding the supporter in position to have the criss-crossed portions exert an elastic pull along the length of the webbing on the opposite upper ends of the pouch, tending to cup the pouch into form-fitting position about the organs and the pubis.*

2. An athletic supporter comprising a waistband or belt of relatively wide *elastic* webbing having a mitre fold directing said webbing adjacent the frontal portion thereof into angularly directed branches following generally the line of the groin, and forming a fold transverse to the axial line of the body *of the wearer, the overlapping and criss-crossing portions above the fold line being substantially free for relative movement of one branch to the other*, [and] a pouch [or sack], the upper edge of which is affixed to said fold, and leg straps for *the opposite end of* said pouch, *the angularly directed branches be-*

*ing substantially free of each other above the fold to effect a criss-crossed elastic pull upon the opposite edge portions of said pouch, tending substantially to cup the pouch by the elastic pull into form-fitting position about the organs.*

[3. In an athletic supporter, a waistband including at its frontal portion a mitre fold, directing said waistband adjacent the frontal portion thereof in an angular direction, and a sack or pouch fastened adjacent said fold.]

[4. In an athletic supporter comprising a waistband or belt of webbing and a sack or pouch fastened at an edge thereof in which said waistband or belt comprises a mitre fold angularly to direct branches adjacent said fold along lines substantially parallel to the groin.]

5. In an athletic supporter comprising a waistband or belt of elastic webbing and a sack or pouch of elastic materials, [of] means to suspend said pouch *from said waistband* comprising a mitre fold providing an edge transverse to the groin, *the webbing above the fold being substantially free for relative movement in distending the elastic webbing along the length of the webbing, the fold being extended for a width substantially equal to the width of the pouch across the groin,* to which *fold* the upper edge of said sack or pouch is affixed, *leaving the waistband free to effect a criss-crossed pull to the opposite edges of the pouch.*

[6. In an athletic supporter comprising a waistband and a sack or pouch supported therefrom, the combination whereof having the waistband of relatively wide webbing formed adjacent the frontal portion thereof with angularly directed apices defining an edge co-terminous with the width of the upper edge of the pouch and to which said pouch is affixed.]

[7. An athletic supporter in accordance with claim 6 wherein a portion of said webbing is formed of elastic fabric.]

[8. An athletic supporter in accordance with claim 6 in which a portion of the webbing of the waistband adjacent the pouch is formed of elastic fabric.]

9. An athletic supporter comprising a *pouch and a* waistband [or be't element] of relatively wide *elastic* webbing [,] formed adjacent the front thereof into angularly, *downwardly* directed branches, each of said branches [having] *terminating in* angularly directed edges, the apices of which overlap *to an extent corresponding substantially to the width of the upper edge of the pouch,* defining an edge transverse to the groin and *having the upper edge of said* [a] pouch [, the upper portion of which is] affixed to the edge of said waistband [aforementioned] *outlined by the overlapping branches of the waistband, to leave the upper section above the transverse edge substantially free for relative movement along the length of the webbing, the overlapping apices effecting a criss-crossed, unrestrained elastic pull over the longitudinal axis of the pouch, tending to cup the pouch into form-fitting position about the organs.*

[10. An athletic supporter comprising a waistband, the frontal portion whereof is formed into downwardly and angularly directed branches following generally the lines of the groin, said branches terminating into mitred sections, the apices of which overlap and provide an edge transverse to the groin to which the pouch portion is affixed, the overlapping apices reinforcing the upper edge of said pouch and being co-terminous with said edge.]

[11. The combination in accordance with claim 10 wherein said webbing includes an elastic insert.]

[12. An athletic supporter comprising a waistband or belt element of relatively wide webbing, the frontal portion thereof being downwardly directed providing spaced branches terminating in mitred edges, the apices of which overlap and define an edge substantially transverse to the groin and a pouch, the upper portion of which is affixed to said edge, the lower portion of which pouch having connected thereto leg straps affixed to the lower edge of said waistband in close adjacency to either side of said pouch.]

FRANCIS H. MONTMARQUET.

REFERENCES CITED

The following references are of record in the file of this patent or the original patent:

UNITED STATES PATENTS

| Number | Name | Date |
|---|---|---|
| 1,155,659 | Johnson | Oct. 5, 1915 |
| 2,137,130 | Cartledge | Nov. 15, 1938 |

FOREIGN PATENTS

| Number | Country | Date |
|---|---|---|
| 494,393 | Great Britain | Oct. 25, 1938 |